(12) United States Patent
Dr. et al.

(10) Patent No.: US 10,330,653 B2
(45) Date of Patent: Jun. 25, 2019

(54) OPTIMIZATION FREE TECHNIQUE FOR DETERMINING UNKNOWN CONCENTRATION OF THE CONSTITUENTS FOR A MIXTURE

(71) Applicant: INDIAN INSTITUTE OF TECHNOLOGY, DELHI, New Delhi (IN)

(72) Inventors: Jayadeva Dr., New Delhi (IN); Sanjit Singh Batra, New Delhi (IN); Munishwar Nath Gupta, New Delhi (IN); Joyeeta Mukherjee, New Delhi (IN)

(73) Assignee: INDIAN INSTITUTE OF TECHNOLOGY, DELHI, New Delhi (IN)

( * ) Notice: Subject to any disclaimer, the term of this patent is extended or adjusted under 35 U.S.C. 154(b) by 189 days.

(21) Appl. No.: 15/123,452

(22) PCT Filed: Mar. 2, 2015

(86) PCT No.: PCT/IB2015/051515
§ 371 (c)(1),
(2) Date: Sep. 2, 2016

(87) PCT Pub. No.: WO2015/132709
PCT Pub. Date: Sep. 11, 2015

(65) Prior Publication Data
US 2017/0074840 A1 Mar. 16, 2017

(30) Foreign Application Priority Data
Mar. 3, 2014 (IN) ............................ 2606/DEL/2013

(51) Int. Cl.
*G06F 11/30* (2006.01)
*G01N 30/86* (2006.01)

(52) U.S. Cl.
CPC ..... *G01N 30/8679* (2013.01); *G01N 30/8693* (2013.01); *G01N 30/8696* (2013.01)

(58) Field of Classification Search
CPC .................................................. G01N 30/8679
See application file for complete search history.

(56) References Cited

U.S. PATENT DOCUMENTS

| | | | | |
|---|---|---|---|---|
| 5,602,755 A | * | 2/1997 | Ashe ................... | G01N 33/2829 702/30 |
| 2006/0101899 A1 | * | 5/2006 | Hastings ............... | G01N 30/18 73/23.41 |
| 2011/0270535 A1 | * | 11/2011 | Sigman .............. | G01N 30/7206 702/28 |

FOREIGN PATENT DOCUMENTS

| | | | |
|---|---|---|---|
| WO | 2011/154258 A1 | 12/2011 | |
| WO | WO 2011/154258 | * | 12/2011 |

OTHER PUBLICATIONS

Jul. 27, 2015 International Search Report issued in International Patent Application No. PCT/IB2015/051515.
(Continued)

*Primary Examiner* — Phuong Huynh
(74) *Attorney, Agent, or Firm* — Oliff PLC

(57) ABSTRACT

The present invention relates to techniques for determining unknown concentration of constituents of any known mixture. The said techniques comprising: obtaining a plurality of chromatograms relating to known concentration of known mixtures and at least one chromatogram relating to unknown concentration of the known mixture; converting each of the chromatograms into signal vectors; condensing the dimensions of each of the signal vectors for obtaining low dimensional signal vectors; processing the low dimensional signal vectors representing the chromatograms relating to known concentrations to obtain output values; and processing the at least one low dimensional signal vector representing the (Continued)

chromatogram relating to unknown concentration by utilizing the obtained output values for determining the unknown concentration of each of the constitutes of the known mixture.

31 Claims, 3 Drawing Sheets

(56) References Cited

OTHER PUBLICATIONS

Sep. 6, 2016 International Preliminary Report on Patentability issued in International Patent Application No. PCT/IB2015/051515.

* cited by examiner

OPTIMIZATION FREE TECHNIQUE FOR DETERMINING UNKNOWN CONCENTRATION OF THE CONSTITUENTS FOR A MIXTURE

FIELD OF THE INVENTION

The present invention generally relates to mixture analysis techniques. More specifically, the present invention relates to an optimization free mixture analysis technique that determines the unknown concentration of the constituents of any given mixture.

BACKGROUND OF THE INVENTION

It is well known that chromatography and electrophoresis are extensively used for estimating concentration of the constituents of a mixture. For instance, analytical chromatography is used for measuring the relative proportions of analytes in a mixture. The essence of all chromatography methods is the partition of analytes between a stationary phase and a mobile phase which elutes through the stationary phase. Further, in high performance liquid chromatography (HPLC), an analyte is generally adsorbed onto an adsorbent in the column. An eluent or solvent selectively removes or displaces analytes from the column, and differences in the partition coefficients result in separation of analytes along the length of the column. The quantity of each analyte is measured as it exits the column, by passing the column output through a detector. The chromatography data is a signal plotted against time (which is generally referred to as chromatogram), where the height of the signal represents the extent of detection of a constituent at that point of time. The type of signal value depends on the type of the detector employed in the analyzer, which exploits a specific physical or chemical property of the mixture.

The area under such a chromatogram gives a measure of the concentration of the constituents. This integrated signal produces the typical chromatogram, which is a plot of signal versus time, and usually appears as a series of peaks. Each peak area yields the amount of the corresponding analyte. The location of the peak indicates the analyte in question. When the peaks are well separated, the areas corresponding to different analytes are distinct and can be correlated well with the amounts of the different analytes in the mixture. However, there are situations where there are unresolved components, as shown in FIG. 1, due to different constituents having similar retention times in the separation column as a result of which they are not fully separated.

In addition, noise may be present which makes it more difficult to separate the peaks. In such a case, the peaks are poorly separated and resolution of areas is difficult or impossible.

Resolution is related to column efficiency, and therefore there is a constant endeavor to increase the efficiency. This is motivated by the fact that higher column efficiency implies improved resolution. Chromatographic efficiency depends on many experimental variables, including temperature, pressure, length of the chromatographic column, and eluent flow rate. Optimizing these variables for a given experiment is a challenging task. Traditional laboratory experiments involve systematic iterations of chromatography, in order to obtain well resolved and separated peaks in a chromatogram. This is tedious and generally time consuming, with no guarantee of success.

Similar is the case with electrophoresis, there are situations where there are unresolved components and for increasing the efficiency, experimental variables such as pH of the buffer, voltage/power employed, length of the gel or time used during electrophoresis have to be optimized. Again optimizing these variables for a given experiment is challenging, tedious and time consuming.

Moreover, in recent years, there have been considerable attempts in employing computational techniques to achieve the optimization task. Early attempts involved using least squares curve fitting. More recent approaches involve optimizing method parameters. Prediction of retention times using support vector machines was also attempted. In the context of gas chromatography, computer simulations to model retention times by using a linear elution strength approximation were also tried. However, such optimization techniques require many experiments and simulations. Further, experiments, when manually conducted, are tedious and time consuming. Moreover, there is no guarantee that the output would be properly separated peaks.

Therefore, there always existed a need in the art to provide a technique for determining the unknown concentration of the constituents of a mixture, that is simple, accurate, easy to implement and at the same time overcomes the above mentioned disadvantages of the prior art.

OBJECTS OF THE INVENTION

An object of the present invention is to provide a method for determining unknown concentration of the constituents of any known mixture.

Another object of the present invention is to provide a system for determining unknown concentration of the constituents of any known mixture.

Yet another object of the present invention is to provide a chromatography apparatus that is located inherent to the system for determining unknown concentration of the constituents of any known mixture.

A further object of the present invention is to provide a chromatography apparatus that is located outside the system for determining unknown concentration of the constituents of any known mixture.

SUMMARY OF THE INVENTION

Accordingly, the present invention relates to a method for determining unknown concentration of constituents of any known mixture, said method comprising: obtaining a plurality of chromatograms relating to known concentration of known mixtures and at least one chromatogram relating to unknown concentration of the known mixture; converting each of the chromatograms into signal vectors; condensing the dimensions of each of the signal vectors for obtaining low dimensional signal vectors; processing the low dimensional signal vectors representing the chromatograms relating to known concentrations to obtain output values; and processing the at least one low dimensional signal vector representing the chromatogram relating to unknown concentration by utilizing the obtained output values for determining the unknown concentration of each of the constitutes of the known mixture.

Further, the present invention relates to a system for determining unknown concentration of constituents of any known mixture, said system comprising: a memory including a converter module, a dimensionality reduction module, a training module, a prediction module, a plurality of chromatograms relating to known concentration of known mixtures, known concentration of mixtures and at least one chromatogram relating to unknown concentration of the known mixture; and a processing unit comprising at least one processor coupled the memory and configured to: obtain, from the memory, a plurality of chromatograms relating to known concentration of known mixtures and at least one chromatogram relating to unknown concentration of the known mixture; execute the converter module for converting each of the chromatograms into signal vectors; execute the dimensionality reduction module for condensing the dimensions of each of the signal vectors for obtaining low dimensional signal vectors; execute the training module for processing the low dimensional signal vectors representing the chromatograms relating to known concentrations to obtain output values; and execute the prediction module for processing the at least one low dimensional signal vector representing the chromatogram relating to unknown concentration by utilizing the obtained output values for determining the unknown concentration of each of the constitutes of the known mixture.

Furthermore, the present invention relates to at least one processor for determining unknown concentration of constituents of any known mixture, comprising: obtaining a plurality of chromatograms relating to known concentration of known mixtures and at least one chromatogram relating to unknown concentration of the known mixture; converting each of the chromatograms into signal vectors; condensing the dimensions of each of the signal vectors for obtaining low dimensional signal vectors; processing the low dimensional signal vectors representing the chromatograms relating to known concentrations to obtain output values; and processing the at least one low dimensional signal vector representing the chromatogram relating to unknown concentration by utilizing the obtained output values for determining the unknown concentration of each of the constitutes of the known mixture.

Also, the present invention relates to a computer readable media embodying a program of instructions executable by one or more processors for determining unknown concentration of constituents of any known mixture, comprising: obtaining a plurality of chromatograms relating to known concentration of known mixtures and at least one chromatogram relating to unknown concentration of the known mixture; converting each of the chromatograms into signal vectors; condensing the dimensions of each of the signal vectors for obtaining low dimensional signal vectors; processing the low dimensional signal vectors representing the chromatograms relating to known concentrations to obtain output values; and processing the at least one low dimensional signal vector representing the chromatogram relating to unknown concentration by utilizing the obtained output values for determining the unknown concentration of each of the constitutes of the known mixture.

Furthermore, the present invention relates to a system for determining unknown concentration of constituents of any known mixture, said system comprising: means for storing a plurality of chromatograms relating to known concentration of known mixtures, known concentration of mixtures and at least one chromatogram relating to unknown concentration of the known mixture; means for obtaining a plurality of chromatograms relating to known concentration of known mixtures and at least one chromatogram relating to unknown concentration of the known mixture; means for converting each of the chromatograms into signal vectors; means for condensing the dimensions of each of the signal vectors for obtaining low dimensional signal vectors; first means for processing the low dimensional signal vectors representing the chromatograms relating to known concentrations to obtain output values; and second means for processing the at least one low dimensional signal vector representing the chromatogram relating to unknown concentration by utilizing the obtained output values for determining the unknown concentration of each of the constitutes of the known mixture.

In the above paragraphs the most important features of the invention have been outlined, in order that the detailed description thereof that follows may be better understood and in order that the present contribution to the art may be better understood and in order that the present contribution to the art may be better appreciated. There are, of course, additional features of the invention that will be described hereinafter and which will form the subject of the claims appended hereto. Those skilled in the art will appreciate that the conception upon which this disclosure is based may readily be utilized as a basis for the designing of other structures for carrying out the several purposes of the invention. It is important therefore that the claims be regarded as including such equivalent constructions as do not depart from the spirit and scope of the invention.

BRIEF DESCRIPTION OF THE DRAWINGS

Further aspects and advantages of the present invention will be readily understood from the following detailed description with reference to the accompanying drawings, where like reference numerals refer to identical or similar or functionally similar elements. The figures together with the detailed description below, are incorporated in and form part of the specification, and serve to further illustrate the aspects/embodiments and explain various principles and advantages, in accordance with the present invention wherein.

Figure 1:
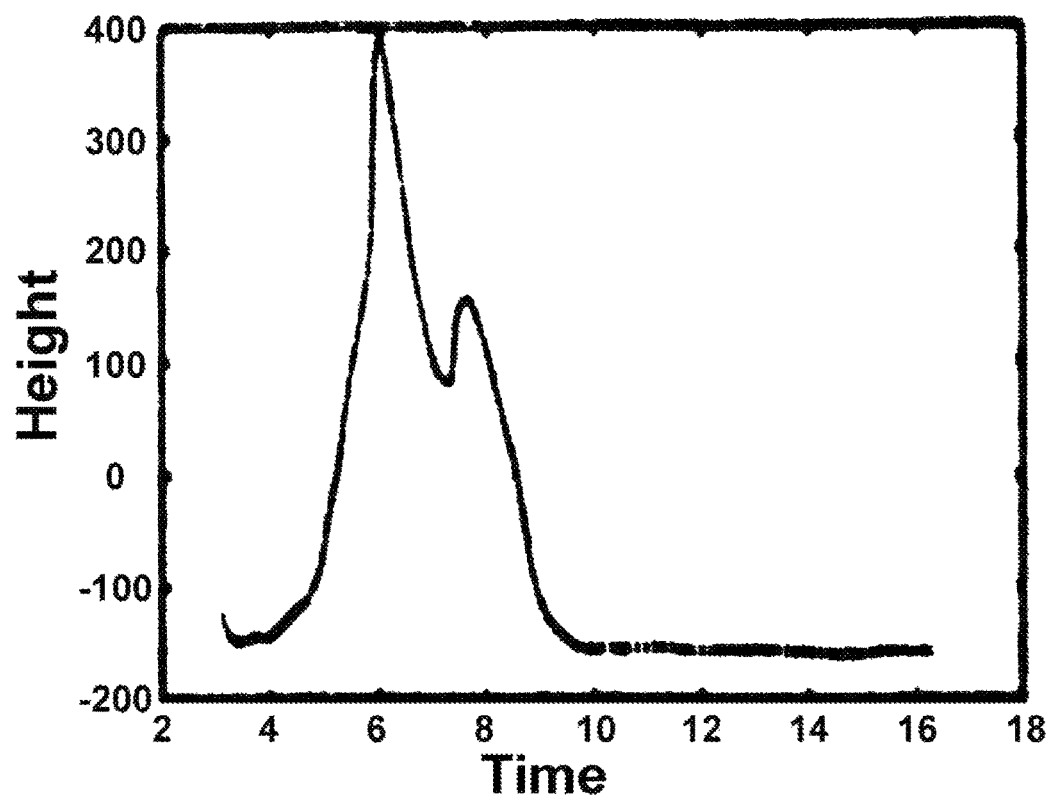
FIG. 1 illustrates a chromatogram showing poorly separated peaks or unresolved peaks.

Skilled artisans will appreciate that elements in the drawings are illustrated for simplicity and have not necessarily been drawn to scale. For example, the dimensions of some of the elements in the drawings may be exaggerated relative to other elements to help to improve understanding of aspects of the present invention.

DETAILED DESCRIPTION OF THE INVENTION

The present invention will be described herein below with reference to the accompanying drawings. In the following description well known functions or constructions are not described in detail since they would obscure the description with unnecessary detail.

According to an aspect of the present invention there is provided a method for determining unknown concentration of constituents of any known mixture, said method comprising: obtaining a plurality of chromatograms relating to known concentration of known mixtures and at least one chromatogram relating to unknown concentration of the known mixture; converting each of the chromatograms into signal vectors; condensing the dimensions of each of the signal vectors for obtaining low dimensional signal vectors; processing the low dimensional signal vectors representing the chromatograms relating to known concentrations to obtain output values; and processing the at least one low dimensional signal vector representing the chromatogram relating to unknown concentration by utilizing the obtained output values for determining the unknown concentration of each of the constitutes of the known mixture.

According to another aspect of the present invention there is provided a method for determining unknown concentration of constituents of any known mixture further comprising: generating chromatograms for the known mixtures by a chromatography apparatus.

According to yet another aspect of the present invention there is provided a method for determining unknown concentration of constituents of any known mixture wherein the step of converting comprises sampling each chromatogram to obtain a signal vector.

According to yet another aspect of the present invention there is provided a method for determining unknown concentration of constituents of any known mixture wherein the step of condensing is performed using techniques such as principle component analysis or linear discriminant analysis or kernel principle component analysis.

According to still another aspect of the present invention there is provided a method for determining unknown concentration of constituents of any known mixture wherein the output values indicate weight vector w, bias constant b and soft-margin slack variables $\xi_i$ and $\hat{\xi}_i$, and wherein the said output values are obtained using the following equation:

Minimize $_{\text{with respect to } w,\xi,\hat{\xi},b}$ $\frac{1}{2}\|w\|^2 + C\Sigma_i(\xi_i + \hat{\xi}_i)$ subject to the constraints $w^T\phi(x_i) + b - \xi_i \leq y_i + \varepsilon$ $w^T\phi(x_i) + b + \hat{\xi}_i \geq y_i - \varepsilon$ $\xi_i \geq 0; \hat{\xi}_i \geq 0, i=1,2,\ldots n$, number of known mixtures of known concentration where: w is the weight vector, b is the bias constant, $y_i$ is the known concentration of the constituents of the known mixtures, $x_i$ is the low dimensional signal vectors corresponding to the chromatograms of known mixtures of known concentration, $\Phi(x_i)$ is the mapping of $x_i$ to a higher dimension, C is a suitably chosen constant, $\xi_i$ and $\hat{\xi}_i$ are soft-margin slack variables, and $\varepsilon$ is a sensitivity parameter.

According to still another aspect of the present invention there is provided a method for determining unknown concentration of constituents of any known mixture wherein the step of processing to determine the unknown concentration comprises implementing the following equation:

$$y = w^T\Phi(x) + b = \sum_i \beta_i K(x_i, x) + b$$

where: w and b are the weight vector and bias constant respectively, x is the low dimensional signal vector corresponding to the chromatogram of the known mixture of unknown concentration, $\Phi$ is the mapping to a higher dimensional space, the second expression is the dual form of the support vector regression formulation, wherein, K $(x_i, x)$ is defined as $\phi(x_i)^T\phi(x)$ and is termed as a Mercer kernel function, $\beta_i$ is a parameter associated with the i'th known mixture of known concentration; i varies over all known mixtures of known concentration; and y is the unknown concentration of the constituents of the known mixture.

According to another aspect of the present invention there is provided a system for determining unknown concentration of constituents of any known mixture, said system comprising: a memory including a converter module, a dimensionality reduction module, a training module, a prediction module, a plurality of chromatograms relating to known concentration of known mixtures, known concentration of mixtures and at least one chromatogram relating to unknown concentration of the known mixture; and a processing unit comprising at least one processor coupled the memory and configured to: obtain, from the memory, a plurality of chromatograms relating to known concentration of known mixtures and at least one chromatogram relating to unknown concentration of the known mixture; execute the converter module for converting each of the chromatograms into signal vectors; execute the dimensionality reduction module for condensing the dimensions of each of the signal vectors for obtaining low dimensional signal vectors; execute the training module for processing the low dimensional signal vectors representing the chromatograms relating to known concentrations to obtain output values; and execute the prediction module for processing the at least one low dimensional signal vector representing the chromatogram relating to unknown concentration by utilizing the obtained output values for determining the unknown concentration of each of the constitutes of the known mixture.

According to another aspect of the present invention there is provided a system for determining unknown concentration of constituents of any known mixture wherein the chromatograms stored in the memory are generated by a chromatography apparatus.

According to yet another aspect of the present invention there is provided a system for determining unknown concentration of constituents of any known mixture wherein the at least one processor is configured to convert each of the chromatograms into signal vectors by sampling each of the chromatograms.

According to yet another aspect of the present invention there is provided a system for determining unknown concentration of constituents of any known mixture wherein the at least one processor is configured to condense the signal vectors into low dimensional signal vectors by using techniques such as principle component analysis or linear discriminant analysis or kernel principle component analysis.

According to yet another aspect of the present invention there is provided a system for determining unknown concentration of constituents of any known mixture wherein the output values indicate weight vector w, bias constant b and soft-margin slack variables $\xi_i$ and $\hat{\xi}_i$, and wherein the at least one processor is configured to obtain said output values by using the following equation:

Minimize $_{\text{with respect to } w,\xi,\hat{\xi},b}$ $\frac{1}{2}\|w\|^2 + C\Sigma_i(\xi_i + \hat{\xi}_i)$ subject to the constraints $w^T\phi(x_i) + b - \xi_i \leq y_i + \varepsilon$ $w^T\phi(x_i) + b + \hat{\xi}_i \geq y_i - \varepsilon$ $\xi_i \geq 0; \hat{\xi}_i \geq 0, i=1,2,\ldots n$, number of known mixtures of known concentration where: w is the weight vector, b is the bias constant, $y_i$ is the known concentration of the constituents of the known mixtures, $x_i$ is the low dimensional signal vectors corresponding to the chromatograms of known mixtures of known concentration, $\Phi(x_i)$ is the mapping of $x_i$ to a higher dimension, C is a suitably chosen constant, $\xi_i$ and $\hat{\xi}_i$ are soft-margin slack variables, and $\varepsilon$ is a sensitivity parameter.

According to still another aspect of the present invention there is provided a system for determining unknown concentration of constituents of any known mixture wherein the at least one processor is configured to determine the unknown concentration by implementing the following equation:

$$y = w^T \Phi(x) + b = \sum_i \beta_i K(x_i, x) + b$$

where:
w and b are the weight vector and bias constant respectively, x is the low dimensional signal vector corresponding to the chromatogram of known mixture of unknown concentration, Φ is the mapping to a higher dimensional space, the second expression is the dual form of the support vector regression formulation, wherein, K ($x_i$, x) is defined as $\phi(x_i)^T \phi(x)$ and is termed as a Mercer kernel function, $\beta_i$ is a parameter associated with the i'th known mixture of known concentration; i varies over all known mixtures of known concentration; and y is unknown concentration of the constituents of the known mixture.

According to a further aspect of the present invention there is provided a system for determining unknown concentration of constituents of any known mixture wherein the chromatography apparatus is coupled to the at least one processor.

According to another further aspect of the present invention there is provided a system for determining unknown concentration of constituents of any known mixture wherein the chromatography apparatus is located inherent to the said system.

According to still further aspect of the present invention there is provided a system for determining unknown concentration of constituents of any known mixture wherein the chromatography apparatus is located outside the said system.

Various embodiments and aspects of the invention will now be described here in detail with reference to the accompanying drawings. The terminology and phraseology used herein is solely for descriptive purposes and should not be construed as limiting in scope. Language such as "including", "comprising", "having", "containing" or "involving", and variations thereof, is intended to be broad and encompass the subject matter listed thereafter, equivalents, and additional subject matter not recited.

Referring now to the figures, there is shown an optimization free technique for determining the unknown concentration of the constituents of any given mixture according to the present invention. It should be understood that the invention is susceptible to various modifications and alternative forms; specific aspects/embodiments thereof have been shown by way of example in the figures and will be described in detail below.

Figure 2:
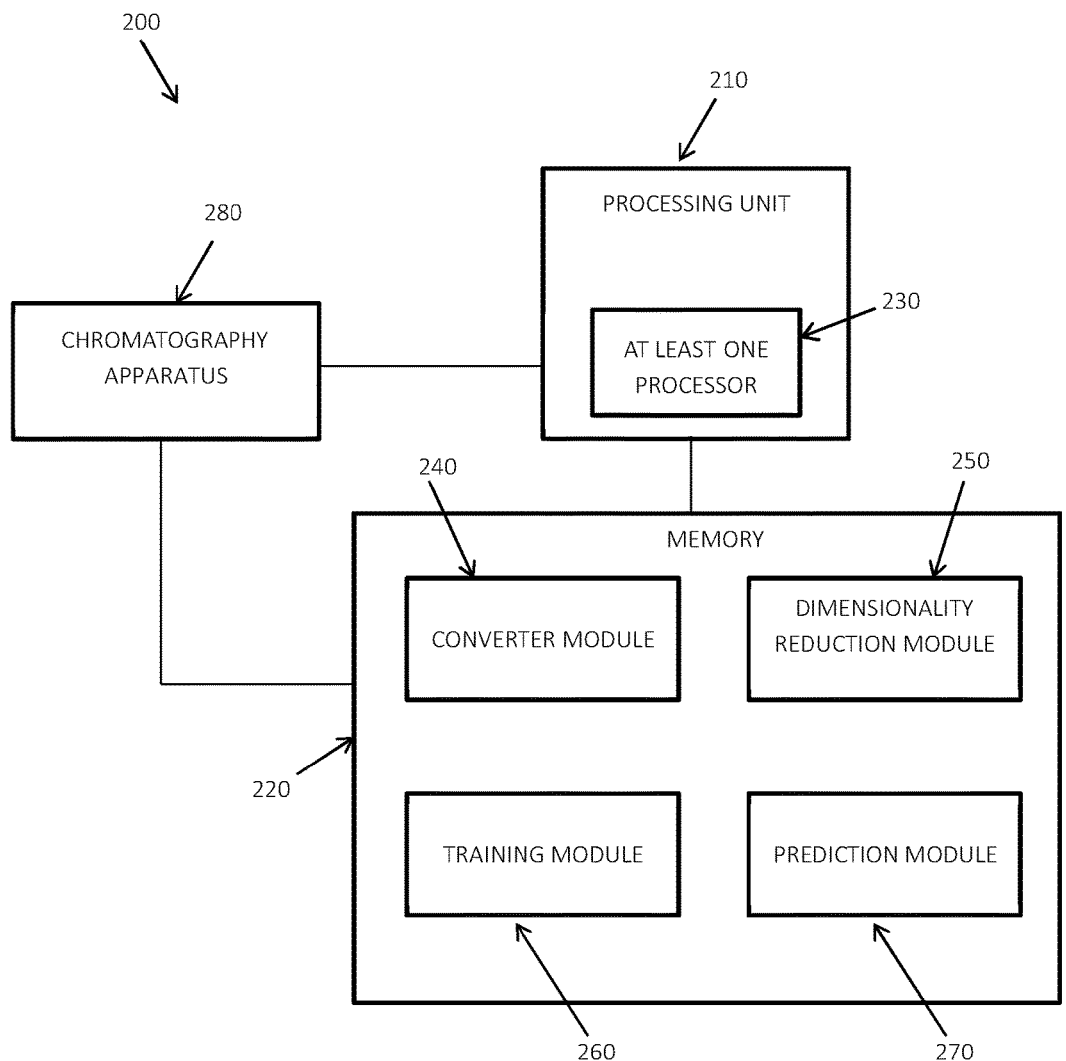
FIG. 2 illustrates the system for determining unknown concentration of the constituents of any given mixture according to an embodiment of the present invention.

FIG. 2 illustrates the system for determining unknown concentration of constituents of any known mixture according to an embodiment of the present invention.

As shown in FIG. 2, the system (200) according to the present invention comprises of a processing unit (210) and a memory (220) operatively coupled to the processing unit (210). In an aspect of this embodiment, the processing unit (210) comprises of at least one processor (230) operatively coupled to the memory (220). The memory (220) comprises of various modules such as converter module (240), dimensionality reduction module (250), training module (260) and prediction module (270).

Further, it can be noticed from FIG. 2, the processing unit (210) and the memory (220) are operatively coupled to a chromatography apparatus (280). In an aspect of this embodiment, the at least one processor (230) and the memory (220) are operatively coupled to the chromatography apparatus (280).

Furthermore, in an aspect of this embodiment, the system (200) of the present invention operates in conjunction with a chromatography apparatus (280) which is located outside the system (200). In this aspect, the apparatus (280) may be an electrophoresis apparatus which is located outside the system (200).

In yet another aspect of this embodiment, the system (200) of the present invention includes a chromatography apparatus (280) operatively coupled to the at least one processor (230). In this aspect, the apparatus (280) may be an electrophoresis apparatus located inherent to the system (200).

It is to be noted that, the system (200) of the present invention can work with any apparatus/device for estimating concentration of the constituents of any known mixture and its application is not only limited to chromatography and electrophoresis.

The memory (220) further includes a plurality of chromatograms (G) relating to known concentration of known mixtures (M) along with the known concentration values of the mixtures (M). The said chromatograms (G) are generated using the chromatography apparatus (280).

Also, the memory (220) includes at least one chromatogram (H) relating to unknown concentration of the same mixture (M). The said chromatogram(s) (H) is/are generated using the chromatography apparatus (280).

The system (200) according to the present invention requires a set of chromatograms (G) (for mixtures (M) for which the concentration of the constituents is known), large enough to represent the underlying distribution of the signal, for training the at least one processor (230) for predicting the unknown concentration of the same mixture (M). Once the chromatograms (G) are generated, data processing performed on the chromatograms (G) enable the at least one processor (230) to learn the relationship between the known concentration of the constituents of a mixture (M) and its corresponding chromatogram (G). Once the at least one processor (230) has learnt the relationship between the known concentration of the constituents of a mixture (M) and its corresponding chromatogram (G), it is able to predict the unknown concentration of the constituents in any other mixture (M) of those very constituents.

This is done by preparing multiple samples (of known concentrations) of the same mixture (M), where each sample is having different concentration of the constituents viz-a-viz the other sample. After preparing different samples, each sample is tested on the chromatography apparatus (280) for obtaining a chromatogram (G). In other words, multiple experiments are conducted with known concentration of specific constituents on the chromatography apparatus (280). Once the multiple chromatograms (G) have been generated, the same are stored in the memory (220). More specifically, the actual (known) concentration of the constituents of a mixture (M) and its corresponding chromatogram (G) is stored in the memory (220).

The at least one processor (230) obtains the chromatograms (G) i.e. the chromatograms relating to known concentration of known mixtures (M) from the memory (220) and executes the converter module (240). The at least one processor (230) executes the converter module (240) for converting each of the chromatograms (G) into signal vectors. A signal vector here represents vector representation of chromatography data with time.

More specifically, the at least one processor (230) executes the converter module (240) for sampling each of the chromatograms (G) for converting them into signal vectors. Each of the signal vectors are in the form of machine readable format data and are stored in the memory (220). In this way, multiple signal vectors are generated corresponding to multiple chromatograms (G).

It is to be noted that the length of the signal vectors obtained are made equal across multiple experiments. The length of each of the signal vectors is usually very large and not amenable to use in raw form. The at least one processor (230) fetches the signal vectors from the memory (220) and executes the dimensionality reduction module (250) for condensing the dimensions of each of the signal vectors for obtaining low dimensional signal vectors. The obtained low dimensional signal vectors are stored in the memory (220).

The dimensionality reduction module (250) implements dimensionality reduction methods to obtain a representation of vectors of smaller lengths that are more amenable to analysis. For example, the dimensionality reduction module (250) uses dimensionality reduction methods such as Principal Components Analysis (PCA) or Linear Discriminant Analysis (LDA) or kernel PCA for condensing the dimensions of signal vectors to obtain a representation of vectors of smaller lengths that are more amenable to analysis. This gives a set of low dimensional signal vectors, each of which corresponds to a chromatogram (G). In a preferred embodiment of the present invention, the dimensionality reduction module (250) uses kernel PCA for obtaining a representation of vectors of smaller lengths.

The at least one processor (230) executes the training module (260) for processing the low dimensional signal vectors representing the chromatograms (G) relating to known concentrations to obtain output values. More specifically, the low dimensional signal vectors corresponding to the chromatograms of known mixtures (M) of known concentration and known concentration values of the constituents of the known mixtures (M) are fed as input to the training module (260). The training module (260) processes the input values to generate output values. The said output values indicate weight vector w, bias constant b and soft-margin slack variables $\xi_i$ and $\hat{\xi}_i$. The output values allows the at least one processor (230) to learn the relationship between a chromatogram (G) and its corresponding concentration values.

The at least one processor (230) obtains the output values by using the following equation:

Minimize $_{with\ respect\ to\ w, \xi, \hat{\xi}, b}$ $\frac{1}{2}\|w\|^2 + C\Sigma_i(\xi_i + \hat{\xi}_i)$ subject to the constraints $w^T\phi(x_i) + b - \xi_i \leq y_i + \varepsilon$ $w^T\phi(x_i) + b + \hat{\xi}_i \geq y_i - \varepsilon$ $\xi_i \geq 0; \hat{\xi}_i \geq 0, i=1,2,\ldots n$, number of known mixtures of known concentration (1)

where:
w is the weight vector; b is the bias constant; $y_i$ is the known concentration of the constituents of the known mixtures; $x_i$ is the low dimensional signal vectors corresponding to the chromatograms of known mixtures of known concentration; $\Phi(x_i)$ is the mapping of $x_i$ to a higher dimension; C is a suitably chosen constant; $\xi_i$ and $\hat{\xi}_i$ are soft-margin slack variables; and $\varepsilon$ is a sensitivity parameter.

The at least one processor (230) solves the above mentioned minimization problem (1) over all possible values of w and b, to learn the relationship between the known concentration values of the constituents of a mixture (M) and its corresponding chromatogram. In this way, the at least one processor (230) is trained to predict/determine the unknown concentration of the constituents in any other known mixture (M) of those very constituents.

The at least one processor (230) obtains from the memory (220) the at least one chromatogram (H) relating to unknown concentration of the same mixture (M). The at least one processor (230) executes the converter module (240) for converting the at least one chromatogram (H) into at least one signal vector. More specifically, the at least one processor (230) executes the converter module (240) for sampling the at least one chromatogram (H) for converting into at least one signal vector. The at least one signal vector obtained is in the form of machine readable format data and is stored in the memory (220).

It is to be noted that the length of the at least one signal vector corresponding to the at least one chromatogram (H) is usually very large and not amenable to use in raw form. The at least one processor (230) fetches the at least one signal vector from the memory (220) and executes the dimensionality reduction module (250) for condensing the dimensions of the at least one signal vector for obtaining at least one low dimensional signal vector. The obtained at least one low dimensional signal vector is stored in the memory (220).

The at least one processor (230) executes the prediction module (270) for processing the at least one low dimensional signal vector representing the at least one chromatograms (H) relating to unknown concentration by utilizing the output values w and b for determining the unknown concentration.

The at least one processor (230) executes the prediction module (270) by implementing the following equation to determine the unknown concentration of the constituents:

$$y = w^T\Phi(x) + b = \sum_i \beta_i K(x_i, x) + b \quad (2)$$

where:
w and b are the weight vector and bias constant respectively as determined above using equation 1; x is the low dimensional signal vector corresponding to the chromatogram of the known mixture of unknown concentration; $\Phi$ is the mapping to a higher dimensional space; the second expression is the dual form of the support vector regression formulation, wherein, K $(x_i, x)$ is defined as $\phi(x_i)^T\phi(x)$ and is termed as a Mercer kernel function; $\beta_i$ is a parameter associated with the i'th known mixture of known concentration; i varies over all known mixtures of known concentration; and y is unknown concentration of the constituents of the known mixture.

In this manner, the at least one processor (230) is able to predict the unknown concentration of the constituents of the mixture (M) using the obtained values w and b. Although, the soft-margin slack variables $\xi_i$ and $\hat{\xi}_i$ are not used in equation 2, their presence plays a critical role in accurate determination of w and b.

Figure 3:
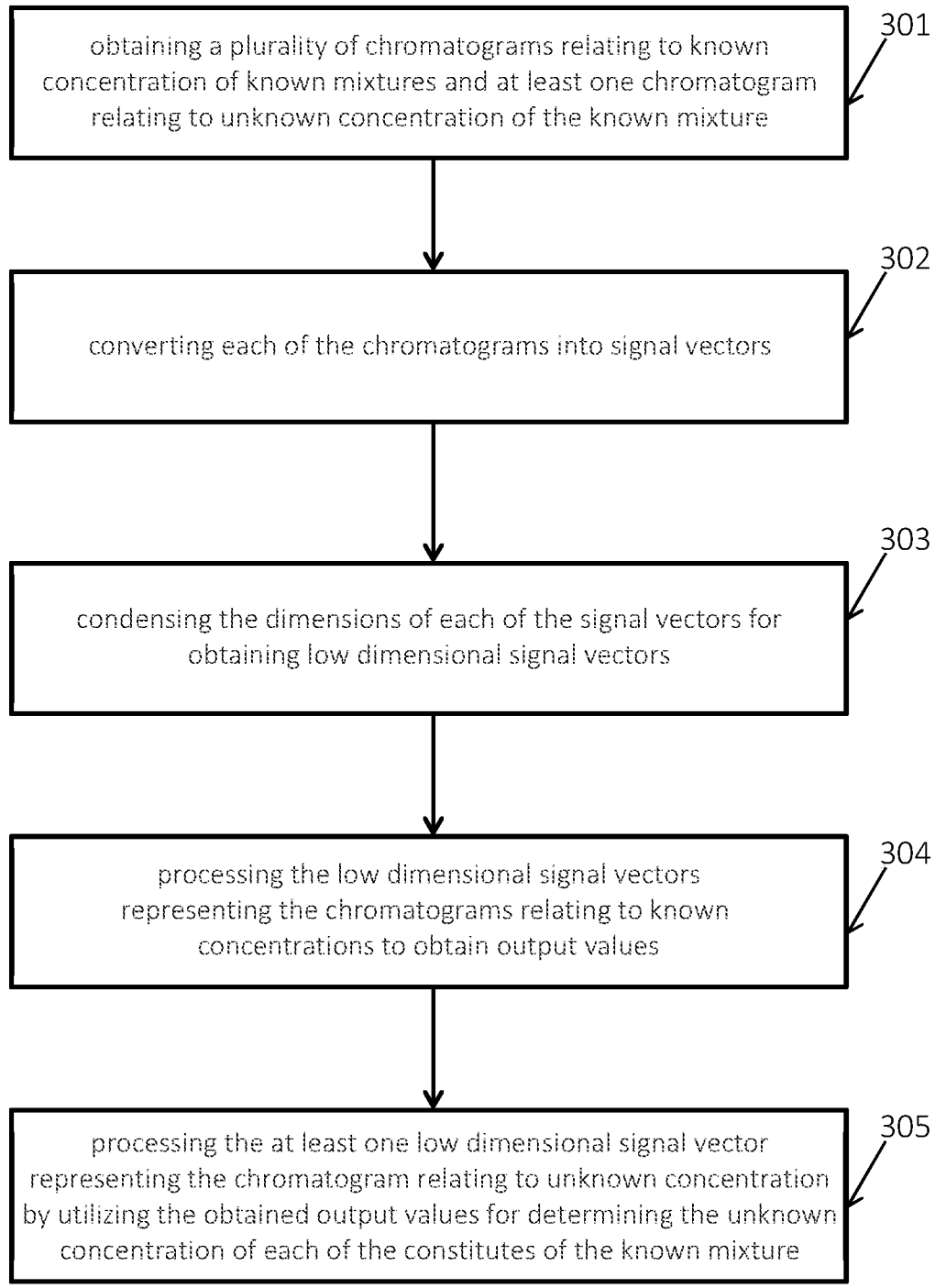
FIG. 3 illustrates the method for determining unknown concentration of the constituents of any given mixture according to an embodiment of the present invention.

FIG. 3 illustrates the method of determining unknown concentration of constituents of any known mixture according to an embodiment of the present invention. In this embodiment, one or more steps shown in FIG. 3 can be omitted, repeated or performed in a different order. Accordingly, the specific arrangements of steps shown in FIG. 3 should not be construed as limiting the scope of the invention.

In step (301), a plurality of chromatograms (G) relating to known concentration of known mixtures (M) and at least one chromatogram (H) relating to unknown concentration of the same known mixture (M) are obtained from the memory (220). The said chromatograms (G) and (H) are generated using the chromatography apparatus (280).

In step (302), each of the chromatograms (G) and (H) is converted into signal vectors. This is done by sampling each of the chromatograms (G) and (H). Each of the signal vectors are in machine readable format data and are stored in the memory (220).

The length of each of the signal vectors is usually very large and not amenable to use in raw form. Thus, in step (303), length of each of the signal vectors is condensed by applying dimensionality reduction methods to obtain a representation of vectors of smaller lengths that are more amenable to analysis. Dimensionality reduction methods, such as Principal Components Analysis (PCA) or Linear Discriminant Analysis or kernel PCA, may be used to obtain a low dimensional approximation. For instance, in the case of PCA, for example, the eigenvalues are used to choose how many principal components to use; this number is usually of the order of 15.

In step (304), the low dimensional signal vectors representing the chromatograms (G) relating to known concentration are processed to obtain output values. For obtaining the output values, the low dimensional signal vectors representing the chromatograms (G) relating to known concentration and known concentration values of the constituents of the mixtures (M) are fetched from the memory (220) and fed as input to the training module (260). The training module (260) processes the input values to generate output values. The said output values indicate weight vector w, bias constant b and soft-margin slack variables $\xi_i$ and $\hat{\xi}_i$.

The output values are obtained by using the following equation:

$$\text{Minimize}_{\text{with respect to } w, \xi, \hat{\xi}, b} \tfrac{1}{2}\|w\|^2 + C\Sigma_i(\xi_i + \hat{\xi}_i)$$

subject to the constraints $$w^T\phi(x_i) + b - \xi_i \leq y_i + \varepsilon$$

$$w^T\phi(x_i) + b + \hat{\xi}_i \geq y_i - \varepsilon$$

$$\xi_i \geq 0; \hat{\xi}_i \geq 0, i=1,2, \ldots n, \text{ number of known mixtures of known concentration} \quad (1)$$

where:
w is the weight vector; b is the bias constant; $y_i$ is the known concentration of the constituents of the known mixtures; $x_i$ is the low dimensional signal vectors corresponding to the chromatograms of known mixtures of known concentration; $\Phi(x_i)$ is the mapping of $x_i$ to a higher dimension; C is a suitably chosen constant; $\xi_i$ and $\hat{\xi}_i$ are soft-margin slack variables; and $\varepsilon$ is a sensitivity parameter.

It is to be noted that, optimization problem (1) is solved separately for every constituent for determining the output values w and b. By solving the above mentioned minimization problem (1) over all possible values of w and b, it is possible to learn the relationship between the known concentration values of the constituents of a mixture (M) and its corresponding chromatogram. In this way, it is possible to predict/determine the unknown concentration of the constituents in any mixture (M) of those very constituents.

Alternatively, in step (304) low dimensional signal vectors are processed in a different manner. For obtaining output values, low dimensional signal vectors representing the chromatograms (G) relating to known concentration and known concentration values of the constituents of the mixtures (M) are fetched from the memory (220) and fed as input to the training module (260). The training module (260) processes the input values to generate output values. The said output values indicate weight matrix W, bias matrix B.

The output values are obtained by using the following equation:

$$\text{Minimize}_{\text{with respect to } W, B} \frac{1}{2}\sum_{j=1}^{q}\|w_j\|^2 + C\sum_{i=1}^{n} L(\|Y_i - W^T\phi(x_i) - B\|) \quad (1')$$

$i=1,2, \ldots n$, number of known mixtures of known concentration and $j=1,2, \ldots q$, number of constituents in a mixture where:
W is the weight matrix having weight vectors (w) as columns; $w_j$ is the weight vector for jth constituent; B is the weight matrix having bias constants (b) as columns; $b_j$ is the bias constant for jth constituent; $Y_i$ is the matrix corresponding to known concentrations of constituents of the ith known mixture, where jth entry in $Y_i$ corresponds to the known concentration of the jth constituent in the ith mixture; $x_i$ is the low dimensional signal vectors corresponding to the chromatograms of known mixtures of known concentration; $\Phi(x_i)$ is the mapping of $x_i$ to a higher dimension; C is a suitably chosen constant; and L is the vapnik $\varepsilon$-insensitive loss function.

By solving the above mentioned minimization problem (1') all possible values of w and b are determined in the matrix form in a single operation. In this way, it is possible to predict/determine the unknown concentration of the constituents using $w_j$ (weight vector for jth constituent) and b (bias constant for jth constituent).

In step (305), the at least one low dimensional signal vector representing the at least one chromatogram (H) relating to unknown concentration is processed by utilizing the output values w and b to determine the unknown concentration.

The processing of the at least one low dimensional signal vector for determining the unknown concentration comprises implementing the following equation:

$$y = w^T\Phi(x) + b = \sum_i \beta_i K(x_i, x) + b \quad (2)$$

where:
w and b are the weight vector and bias constant respectively as determined above using equation 1; x is the low dimensional signal vector corresponding to the chromatogram of unknown concentration; $\Phi$ is the mapping to a higher dimensional space; the second expression is the dual form of the support vector regression formulation, wherein, $K(x_i, x)$ is defined as $\phi(x_i)^T\phi(x)$ and is termed as a Mercer kernel function; $\beta_i$ is a parameter associated with the i'th known mixture of known concentration; i varies over all known mixtures of known concentration; and y is unknown concentration of the constituents of the known mixture.

The procedure of the present invention can be better understood with the help of the following example/experiment illustrated below:

Reference is given to the constituents/analytes as A and B. Chromatograms with analyte A alone and B alone were generated using six choices of concentration of each, namely 25, 50, 70, 100, 120, and 150. The chromatogram was obtained as a comma separated value (csv) file. This file contains a large number of time samples, and is not suitable for use in its raw form. The lengths of different chromatograms are different, and to obviate this problem, the samples are binned using bins corresponding to intervals of 0.1 s each. The signal value at each bin location is the average of the samples in the bin. Each chromatogram is thus converted to a time series of about 3000 samples. The time series is treated as a single vector. The vectors corresponding to different concentrations of A and B form the training data. However, data consisting of 3000 dimensional vectors is not amenable to usage, and thus requires further processing.

Principal components of the data so obtained were computed. Typically, it was found that, the first 10 eigenvectors or so contain about 99% of the signal energy. On computing the first 15 principal components, the present system obtained the projections of the time series vectors in these directions. Thus, each chromatogram is now represented as a 15 dimensional vector. The 15 dimensional vectors form inputs to the at least one processor. The at least one processor learnt the concentration of A and concentration of B.

Chromatograms corresponding to mixtures of A and B were then fed as inputs to the trained at least one processor. The output of the at least one processor yields the required estimates of the amounts of constituents/analytes A and B.

Table 1 shows the actual and predicted concentrations of A and B for a set of 3 experiments.

TABLE 1

| S. No | Actual conc. of A | Actual conc. of B | Predicted conc. of A | Predicted conc. of B |
|---|---|---|---|---|
| 1 | 7.5 mM | 10 mM | 8.1 mM | 10.2 mM |
| 2 | 5.0 mM | 5.0 mM | 4.7 mM | 5.2 mM |
| 3 | 2.5 mM | 2.5 mM | 2.4 mM | 2.6 mM |

Table 1 shows that accurate estimates can be obtained with small amounts of data. The table also shows that despite not using mixtures of A and B in the training data, the error is small. It is pertinent to point out that the accuracy can be further improved by increasing the amount of training data.

Further, it is pertinent to note that, the proposed technique can be used in other related contexts, such as for estimating the fractions of different enantiomers of the same analyte in a chiral column. Table 2 shows the actual and predicted concentrations of two enantiomers of Phenyl ethylamine for a set of 3 experiments. Referring to the enantiomers as R and S, the training was performed on 6 samples of concentration of each, R and S, as well as 3 samples of R and S together. Table 2 shows that accurate estimates can be obtained with small amounts of data.

TABLE 2

| S. No | Actual conc. of A | Actual conc. of B | Predicted conc. of A | Predicted conc. of B |
|---|---|---|---|---|
| 1 | 30 ml/L | 30 ml/L | 28 ml/L | 27 ml/L |
| 2 | 40 ml/L | 40 ml/L | 39 ml/L | 43 ml/L |
| 3 | 30 ml/L | 15 ml/L | 33 ml/L | 35 ml/L |

To conclude, the aforesaid methodology eliminates the need to systematically deduce ideal conditions for a resolved chromatogram. The methodology according to the present invention requires a set of chromatograms (for mixtures for which the concentration of the constituents is known), large enough to represent the underlying distribution of the signal, for training a system for predicting the unknown concentrations. Once the chromatograms are generated, data processing performed on these chromatograms enable the system to learn the relationship between the known concentration of the constituents of a mixture and its corresponding chromatogram. Once the system has learnt the relationship between the known concentration of the constituents and its corresponding chromatogram, it is able to predict the unknown concentration of the constituents in any other mixture of those very constituents. The aforesaid technique can be adopted for use in a variety of chromatographic methods, as well as in electrophoresis, and in other processes used for estimation of concentration of the constituents of a mixture. Also, the methodology of the present invention can be used in applications such as ChIP-sequence experimental data, or RNA sequencing data, DNA Microarray data, etc.

The presentation of the configurations described herein is provided to enable any person skilled in the art to make or use the methods and other structures disclosed herein. The flowcharts, block diagrams, and other structures shown and described herein are examples only, and other variants of these structures are also within the scope of the disclosure. Various modifications to these configurations are possible, and the generic principles presented herein may be applied to other configurations as well. Thus, the present disclosure is not intended to be limited to the configurations shown above but rather is to be accorded the widest scope consistent with the principles and novel features disclosed in any fashion herein.

The various elements of an implementation of an apparatus as disclosed herein may be embodied in any hardware structure, or any combination of hardware with software and/or firmware, that is deemed suitable for the intended application. One or more elements of the various implementations of the apparatus disclosed herein may also be implemented in part as one or more sets of instructions arranged to execute on one or more fixed or programmable arrays of logic elements, such as microprocessors, embedded processors, IP cores, digital signal processors, FPGAs (field-programmable gate arrays), ASSPs (application-specific standard products), and ASICs (application-specific integrated circuits).

A processor or means as disclosed herein may be fabricated as one or more electronic and/or optical devices residing, for example, on the same chip or among two or more chips in a chipset. One example of such a device is a fixed or programmable array of logic elements, such as transistors or logic gates, and any of these elements may be implemented as one or more such arrays. Such an array or arrays may be implemented within one or more chips (for example, within a chipset including two or more chips). Examples of such arrays include fixed or programmable arrays of logic elements, such as microprocessors, embedded processors, IP cores, DSPs, FPGAs, ASSPs, and ASICs. A processor or means as disclosed herein may also be embodied as one or more computers (e.g., machines including one or more arrays programmed to execute one or more sets or sequences of instructions) or other processors.

Those of skill will appreciate that the various illustrative modules, logical blocks, means and other operations described in connection with the configurations disclosed herein may be implemented as electronic hardware, computer software, or combinations of both. In hardware implementation, such modules, logical blocks, means and operations may be implemented as a general purpose processor, a digital signal processor (DSP), an ASIC or ASSP, an FPGA or other programmable logic device, discrete gate or transistor logic, discrete hardware components, or any combination thereof designed to produce the configuration as disclosed herein.

For a software implementation, the techniques described herein may be implemented with modules (e.g., procedures, functions, and so on) that perform the functions described herein. The software codes may be stored in a memory unit and executed by a processor. The memory unit may be implemented within the processor or external to the processor, in which case it can be communicatively coupled to the processor via various means as is known in the art.

It is noted that the various methods disclosed herein may be performed by an array of logic elements such as a processor. Each of the tasks of the methods described herein may be embodied directly in hardware, in a software module executed by a processor, or in a combination of the two.

It is to be noted that computer-readable medium can comprise a data storage medium such as RAM, such as synchronous dynamic random access memory (SDRAM), read-only memory (ROM), non-volatile random access memory (NVRAM), ROM, electrically erasable programmable read-only memory (EEPROM), EEPROM, FLASH memory, CD-ROM or other optical disk storage, magnetic disk storage or other magnetic storage devices, or any other computer-readable data storage medium that can be used to carry or store desired program code in the form of instructions or data structures and that can be accessed by a computer/processor.

The foregoing detailed description has described only a few of the many possible implementations of the present invention. Thus, the detailed description is given only by way of illustration and nothing contained in this section should be construed to limit the scope of the invention. The claims are limited only by the following claims, including the equivalents thereof.

The invention claimed is:

1. A method for determining unknown concentration of constituents of any known mixture, said method comprising:
   obtaining a plurality of chromatograms relating to known concentration of known mixtures and at least one chromatogram relating to unknown concentration of the known mixture;
   converting each of the chromatograms into signal vectors;
   condensing the dimensions of each of the signal vectors for obtaining low dimensional signal vectors;
   processing the low dimensional signal vectors representing the chromatograms relating to known concentrations to obtain output values; and
   processing the at least one low dimensional signal vector representing the chromatogram relating to unknown concentration by utilizing the obtained output values for determining the unknown concentration of each of the constitutes of the known mixture.

2. The method as claimed in claim 1, further comprising the step of:
   generating chromatograms for the mixtures by a chromatography apparatus.

3. The method as claimed in claim 1, wherein the step of converting comprises sampling each chromatogram to obtain a signal vector.

4. The method as claimed in claim 1, wherein the step of condensing is performed using techniques such as principle component analysis or linear discriminant analysis or kernel principle component analysis.

5. The method as claimed in claim 1, wherein the output values indicate weight vector w, bias constant b and soft-margin slack variables $\xi_i$ and $\hat{\xi}_i$, and wherein the said output values are obtained using the following equation:

$$\text{Minimize}_{\text{with respect to } w, \xi, \hat{\xi}, b} \tfrac{1}{2}\|w\|^2 + C\Sigma_i(\xi_i + \hat{\xi}_i)$$

subject to the constraints $$w^T\phi(x_i) + b - \xi_i \leq y_i + \varepsilon$$

$$w^T\phi(x_i) + b + \hat{\xi}_i \geq y_i - \varepsilon$$

$$\xi_i \geq 0; \hat{\xi}_i \geq 0, i = 1, 2, \ldots n, \text{ number of known mixtures of known concentration}$$

where:
w is the weight vector, b is the bias constant, $y_i$ is the known concentration of the constituents of the known mixtures, $x_i$ is the low dimensional signal vectors corresponding to the chromatograms of known mixtures of known concentration, $\Phi(x_i)$ is the mapping of $x_i$ to a higher dimension, C is a suitably chosen constant, $\xi_i$ and $\hat{\xi}_i$ are soft-margin slack variables, and $\varepsilon$ is a sensitivity parameter.

6. The method as claimed in claim 5, wherein the step of processing to determine the unknown concentration comprises implementing the following equation:

$$y = w^T\Phi(x) + b = \sum_i \beta_i K(x_i, x) + b$$

where:
w and b are the weight vector and bias constant respectively, x is the low dimensional signal vector corresponding to the chromatogram of known mixture of unknown concentration, $\Phi$ is the mapping to a higher dimensional space, the second expression is the dual form of the support vector regression formulation, wherein, K $(x_i, x)$ is defined as $\phi(x_i)^T\phi(x)$ and is termed as a Mercer kernel function, $\beta_i$ is a parameter associated with the i'th known mixture of known concentration; i varies over all known mixtures of known concentration; and y is unknown concentration of the constituents of the known mixture.

7. A system for determining unknown concentration of constituents of any known mixture, said system comprising:
   a memory including a converter module, a dimensionality reduction module, a training module, a prediction module, a plurality of chromatograms relating to known concentration of known mixtures, known concentration of mixtures and at least one chromatogram relating to unknown concentration of the known mixture; and
   a processing unit comprising at least one processor coupled the memory and configured to:
   obtain, from the memory, a plurality of chromatograms relating to known concentration of known mixtures and at least one chromatogram relating to unknown concentration of the known mixture;
   execute the converter module for converting each of the chromatograms into signal vectors;
   execute the dimensionality reduction module for condensing the dimensions of each of the signal vectors for obtaining low dimensional signal vectors;

execute the training module for processing the low dimensional signal vectors representing the chromatograms relating to known concentrations to obtain output values; and execute the prediction module for processing the at least one low dimensional signal vector representing the chromatogram relating to unknown concentration by utilizing the obtained output values for determining the unknown concentration of each of the constitutes of the known mixture.

8. The system as claimed in claim 7, wherein the chromatograms are generated by a chromatography apparatus.

9. The system as claimed in claim 7, wherein the at least one processor is configured to convert each of the chromatograms into signal vectors by sampling each of the chromatograms.

10. The system as claimed in claim 7, wherein the at least one processor is configured to condense the signal vectors into low dimensional signal vectors by using techniques such as principle component analysis or linear discriminant analysis or kernel principle component analysis.

11. The system as claimed in claim 7, wherein the output values indicate weight vector w, bias constant b and soft-margin slack variables $\xi_i$ and $\hat{\xi}_i$, and wherein the at least one processor is configured to obtain said output values by using the following equation:

$$\text{Minimize}_{\text{with respect to } w, \xi, \hat{\xi}, b} \tfrac{1}{2}\|w\|^2 + C\Sigma_i(\xi_i + \hat{\xi}_i)$$

subject to the constraints $$w^T\phi(x_i) + b - \xi_i \leq y_i + \varepsilon$$

$$w^T\phi(x_i) + b + \hat{\xi}_i \geq y_i - \varepsilon$$

$\xi_i \geq 0; \hat{\xi}_i \geq 0, i=1,2,\ldots n$, number of known mixtures of known concentration where:

w is the weight vector, b is the bias constant, $y_i$ is the known concentration of the constituents of the known mixtures, $x_i$ is the low dimensional signal vectors corresponding to the chromatograms of known mixtures of known concentration, $\Phi(x_i)$ is the mapping of $x_i$ to a higher dimension, C is a suitably chosen constant, $\xi_i$ and $\hat{\xi}_i$ are soft-margin slack variables, and $\varepsilon$ is a sensitivity parameter.

12. The system as claimed in claim 11, wherein the at least one processor is configured to determine the unknown concentration by implementing the following equation:

$$y = w^T\Phi(x) + b = \Sigma\beta_i K(x_i, x) + b$$

where:

w and b are the weight vector and bias constant respectively, x is the low dimensional signal vector corresponding to the chromatogram of the known mixture of unknown concentration, $\Phi$ is the mapping to a higher dimensional space, the second expression is the dual form of the support vector regression formulation, wherein, K ($x_i$, x) is defined as $\phi(x_i)^T\phi(x)$ and is termed as a Mercer kernel function, $\beta_i$ is a parameter associated with the i'th known mixture of known concentration; i varies over all known mixtures of known concentration; and y is unknown concentration of the constituents of the known mixture.

13. The system as claimed in claim 8, wherein the chromatography apparatus is coupled to the at least one processor.

14. The system as claimed in claim 8, wherein the chromatography apparatus is located inherent to the said system.

15. The system as claimed in claim 8, wherein the chromatography apparatus is located outside the said system.

16. At least one processor for determining unknown concentration of constituents of any known mixture, comprising:

obtaining a plurality of chromatograms relating to known concentration of known mixtures and at least one chromatogram relating to unknown concentration of the known mixture;

converting each of the chromatograms into signal vectors;

condensing the dimensions of each of the signal vectors for obtaining low dimensional signal vectors;

processing the low dimensional signal vectors representing the chromatograms relating to known concentrations to obtain output values; and processing the at least one low dimensional signal vector representing the chromatogram relating to unknown concentration by utilizing the obtained output values for determining the unknown concentration of each of the constitutes of the known mixture.

17. The at least one processor as claimed in claim 16, wherein converting comprises sampling each chromatogram to obtain a signal vector.

18. The at least one processor as claimed in claim 16, wherein condensing is performed using techniques such as principle component analysis or linear discriminant analysis or kernel principle component analysis.

19. The at least one processor as claimed in claim 16, wherein the output values indicate weight vector w, bias constant b and soft-margin slack variables $\xi_i$ and $\hat{\xi}_i$, and wherein the said output values are obtained using the following equation:

$$\text{Minimize}_{\text{with respect to } w, \xi, \hat{\xi}, b} \tfrac{1}{2}\|w\|^2 + C\Sigma_i(\xi_i + \hat{\xi}_i)$$

subject to the constraints $$w^T\phi(x_i) + b - \xi_i \leq y_i + \varepsilon$$

$$w^T\phi(x_i) + b + \hat{\xi}_i \geq y_i - \varepsilon$$

$\xi_i \geq 0; \hat{\xi}_i \geq 0, i=1,2,\ldots n$, number of known mixtures of known concentration where:

w is the weight vector, b is the bias constant, $y_i$ is the known concentration of the constituents of the known mixtures, $x_i$ is the low dimensional signal vectors corresponding to the chromatograms of known mixtures of known concentration, $\Phi(x_i)$ is the mapping of $x_i$ to a higher dimension, C is a suitably chosen constant, $\xi_i$ and $\hat{\xi}_i$ are soft-margin slack variables, and $\varepsilon$ is a sensitivity parameter.

20. The at least one processor as claimed in claim 19, wherein processing to determine the unknown concentration comprises implementing the following equation:

$$y = w^T\Phi(x) + b = \sum_i \beta_i K(x_i, x) + b$$

where:

w and b are the weight vector and bias constant respectively, x is the low dimensional signal vector corresponding to the chromatogram of known mixture of unknown concentration, Φ is the mapping to a higher dimensional space, the second expression is the dual form of the support vector regression formulation, wherein, K ($x_i$, x) is defined as $\phi(x_i)^T\phi(x)$ and is termed as a Mercer kernel function, $\beta_i$ is a parameter associated with the i'th known mixture of known concentration; i varies over all known mixtures of known concentration; and y is unknown concentration of the constituents of the known mixture.

21. A non-transitory computer readable media embodying a program of instructions executable by one or more processors for determining unknown concentration of constituents of any known mixture, comprising:

obtaining a plurality of chromatograms relating to known concentration of known mixtures and at least one chromatogram relating to unknown concentration of the known mixture;

converting each of the chromatograms into signal vectors;

condensing the dimensions of each of the signal vectors for obtaining low dimensional signal vectors;

processing the low dimensional signal vectors representing the chromatograms relating to known concentrations to obtain output values; and processing the at least one low dimensional signal vector representing the chromatogram relating to unknown concentration by utilizing the obtained output values for determining the unknown concentration of each of the constitutes of the known mixture.

22. The non-transitory computer readable media as claimed in claim 21, wherein converting comprises sampling each chromatogram to obtain a signal vector.

23. The non-transitory computer readable media as claimed in claim 21, wherein condensing is performed using techniques such as principle component analysis or linear discriminant analysis or kernel principle component analysis.

24. The non-transitory computer readable media as claimed in claim 21, wherein the output values indicate weight vector w, bias constant b and soft-margin slack variables $\xi_i$ and $\hat{\xi}_i$, and wherein the said output values are obtained using the following equation:

$$\text{Minimize}_{\text{with respect to } w,\xi,\hat{\xi},b} \tfrac{1}{2}\|w\|^2 + C\Sigma_i(\xi_i + \hat{\xi}_i)$$

subject to the constraints $$w^T\phi(x_i)+b-\xi_i \leq y_i+\varepsilon$$

$$w^T\phi(x_i)+b+\hat{\xi}_i \geq y_i-\varepsilon$$

$\xi_i \geq 0; \hat{\xi}_i \geq 0, i=1,2, \ldots n$, number of known mixtures of known concentration where:

w is the weight vector, b is the bias constant, $y_i$ is the known concentration of the constituents of the known mixtures, $x_i$ is the low dimensional signal vectors corresponding to the chromatograms of known mixtures of known concentration, $\Phi(x_i)$ is the mapping of $x_i$ to a higher dimension, C is a suitably chosen constant, $\xi_i$ and $\hat{\xi}_i$ are soft-margin slack variables, and ε is a sensitivity parameter.

25. The non-transitory computer readable media as claimed in claim 24, wherein processing to determine the unknown concentration comprises implementing the following equation:

$$y = w^T\Phi(x) + b = \sum_i \beta_i K(x_i, x) + b$$

where:

w and b are the weight vector and bias constant respectively, x is the low dimensional signal vector corresponding to the chromatogram of known mixture of unknown concentration, Φ is the mapping to a higher dimensional space, the second expression is the dual form of the support vector regression formulation, wherein, K ($x_i$, x) is defined as $\phi(x_i)^T\phi(x)$ and is termed as a Mercer kernel function, $\beta_i$ is a parameter associated with the i'th known mixture of known concentration; i varies over all known mixtures of known concentration; and y is unknown concentration of the constituents of the known mixture.

26. A system for determining unknown concentration of constituents of any known mixture, said system comprising:

means for storing a plurality of chromatograms relating to known concentration of known mixtures, known concentration of mixtures and at least one chromatogram relating to unknown concentration of the known mixture;

means for obtaining a plurality of chromatograms relating to known concentration of known mixtures and at least one chromatogram relating to unknown concentration of the known mixture;

means for converting each of the chromatograms into signal vectors;

means for condensing the dimensions of each of the signal vectors for obtaining low dimensional signal vectors;

first means for processing the low dimensional signal vectors representing the chromatograms relating to known concentrations to obtain output values; and second means for processing the at least one low dimensional signal vector representing the chromatogram relating to unknown concentration by utilizing the obtained output values for determining the unknown concentration of each of the constitutes of the known mixture.

27. The system as claimed in claim 26, wherein the chromatograms are generated by a chromatography apparatus.

28. The system as claimed in claim 26, wherein the means for converting each of the chromatograms into signal vectors comprises means for sampling each of the chromatograms.

29. The system as claimed in claim 26, wherein the means for condensing is configured to condense signal vectors into low dimensional signal vectors by using techniques such as principle component analysis or linear discriminant analysis or kernel principle component analysis.

30. The system as claimed in claim 26, wherein the output values indicate weight vector w, bias constant b and soft-margin slack variables $\xi_i$ and $\hat{\xi}_i$, and wherein the first means for processing comprises means for obtaining said output values by using the following equation:

$$\text{Minimize}_{\text{with respect to } w,\xi,\hat{\xi},b} \tfrac{1}{2}\|w\|^2 + C\Sigma_i(\xi_i + \hat{\xi}_i)$$

subject to the constraints $$w^T\phi(x_i)+b-\xi_i \leq y_i+\varepsilon$$

$$w^T\phi(x_i)+b+\hat{\xi}_i \geq y_i-\varepsilon$$

$\xi_i \geq 0; \hat{\xi}_i \geq 0, i=1,2, \ldots n$, number of known mixtures of known concentration where:
w is the weight vector, b is the bias constant, $y_i$ is the known concentration of the constituents of the known mixtures, $x_i$ is the low dimensional signal vectors corresponding to the chromatograms of known mixtures of known concentration, $\Phi(x_i)$ is the mapping of $x_i$ to a higher dimension, C is a suitably chosen constant, $\xi_i$ and $\hat{\xi}_i$ are soft-margin slack variables, and $\varepsilon$ is a sensitivity parameter.

31. The system as claimed in claim 30, wherein the second means for processing is configured to determine the unknown concentration by implementing the following equation:

$$y = w^T \Phi(x) + b = \sum_i \beta_i K(x_i, x) + b$$

where:
w and b are the weight vector and bias constant respectively, x is the low dimensional signal vector corresponding to the chromatogram of the known mixture of unknown concentration, $\Phi$ is the mapping to a higher dimensional space, the second expression is the dual form of the support vector regression formulation, wherein, $K(x_i, x)$ is defined as $\phi(x_i)^T \phi(x)$ and is termed as a Mercer kernel function, $\beta_i$ is a parameter associated with the i'th known mixture of known concentration; i varies over all known mixtures of known concentration; and y is unknown concentration of the constituents of the known mixture.

* * * * *